US010123791B2

(12) United States Patent
Whitman

(10) Patent No.: US 10,123,791 B2
(45) Date of Patent: Nov. 13, 2018

(54) LIGHTED POLYHEDRAL RETRACTOR

(71) Applicant: Atlantic Health System, Inc., Morristown, NJ (US)

(72) Inventor: Eric D. Whitman, Mountain Lakes, NJ (US)

(73) Assignee: Atlantic Health System, Inc., Morristown, NJ (US)

( * ) Notice: Subject to any disclaimer, the term of this patent is extended or adjusted under 35 U.S.C. 154(b) by 237 days.

(21) Appl. No.: 14/791,095

(22) Filed: Jul. 2, 2015

(65) Prior Publication Data

US 2017/0000470 A1    Jan. 5, 2017

(51) Int. Cl.
*A61B 1/32*    (2006.01)
*A61B 17/02*    (2006.01)
*A61B 90/30*    (2016.01)

(52) U.S. Cl.
CPC .......... *A61B 17/0218* (2013.01); *A61B 90/30* (2016.02)

(58) Field of Classification Search
CPC . A61B 17/02; A61B 17/0218; A61B 17/0281; A61B 1/32; A61B 90/30
See application file for complete search history.

(56) References Cited

U.S. PATENT DOCUMENTS

| | | | | |
|---|---|---|---|---|
| 3,774,596 A | * | 11/1973 | Cook | A61B 1/31 600/184 |
| 4,942,700 A | * | 7/1990 | Hoberman | E04B 1/3211 52/109 |
| 5,024,031 A | * | 6/1991 | Hoberman | E04B 1/3211 52/109 |
| 5,275,610 A | * | 1/1994 | Eberbach | A61M 29/02 604/105 |
| 5,402,772 A | | 4/1995 | Moll | |
| 5,522,790 A | * | 6/1996 | Moll | A61B 17/0218 600/204 |
| 5,527,264 A | * | 6/1996 | Moll | A61B 17/0218 600/204 |
| 5,562,603 A | * | 10/1996 | Moll | A61B 17/0218 600/204 |
| 5,738,629 A | * | 4/1998 | Moll | A61B 17/00234 600/116 |
| 5,743,850 A | * | 4/1998 | Moll | A61B 17/00234 600/204 |
| 5,743,851 A | * | 4/1998 | Moll | A61B 17/0218 600/116 |
| 5,761,871 A | * | 6/1998 | Atake | E04B 1/32 52/109 |
| 5,823,945 A | * | 10/1998 | Moll | A61B 17/00234 600/204 |
| 6,605,037 B1 | * | 8/2003 | Moll | A61B 17/0218 600/204 |
| 7,556,601 B2 | | 7/2009 | Branch | |
| 7,625,339 B2 | | 12/2009 | Frasier | |
| 7,766,823 B2 | * | 8/2010 | Moll | A61B 17/0218 600/192 |
| 7,909,761 B2 | | 3/2011 | Banchieri | |

(Continued)

*Primary Examiner* — Jacqueline Johanas
(74) *Attorney, Agent, or Firm* — The McHattie Law Firm; Jonathan A. Tyler

(57) ABSTRACT

The present invention provides a surgical retractor that provides improved access to a surgical space, devised in the shape of a partial polyhedron, and also provides improved visualization of the surgical space with light emitting elements placed within the polyhedron structure.

5 Claims, 5 Drawing Sheets

(56) References Cited

U.S. PATENT DOCUMENTS

| | | | |
|---|---|---|---|
| 7,922,658 B2 | 4/2011 | Cohen | |
| 8,075,582 B2 | 12/2011 | Lointier | |
| 9,259,233 B2* | 2/2016 | Gruber | A61B 1/303 |
| 9,307,972 B2* | 4/2016 | Lovell | A61B 17/0206 |
| 2003/0095781 A1 | 5/2003 | Williams | |
| 2004/0097792 A1* | 5/2004 | Moll | A61B 17/0218 600/201 |
| 2004/0236186 A1 | 11/2004 | Chu | |
| 2005/0273133 A1* | 12/2005 | Shluzas | A61B 17/3439 606/198 |
| 2006/0189849 A1* | 8/2006 | Sharratt | A61B 1/32 600/249 |
| 2007/0088436 A1* | 4/2007 | Parsons | A61B 17/7098 623/17.11 |
| 2008/0249534 A1* | 10/2008 | Gruber | A61B 1/303 606/119 |
| 2009/0112068 A1* | 4/2009 | Grey | A61B 17/02 600/212 |
| 2009/0287046 A1* | 11/2009 | Yamatani | A61B 17/0218 600/104 |
| 2010/0030033 A1* | 2/2010 | Farley | A61B 1/07 600/249 |
| 2010/0174149 A1* | 7/2010 | Moll | A61B 17/0218 600/203 |
| 2010/0318121 A1* | 12/2010 | Levin | A61B 17/00491 606/213 |
| 2012/0035502 A1* | 2/2012 | Menegazzi | A61B 1/0008 600/567 |
| 2012/0296171 A1* | 11/2012 | Lovell | A61B 17/0206 600/213 |
| 2013/0150677 A1* | 6/2013 | Miles | A61B 17/02 600/202 |
| 2013/0296655 A1* | 11/2013 | Hart | A61B 17/0293 600/208 |
| 2014/0031630 A1* | 1/2014 | Nguyen | A61B 17/0218 600/204 |
| 2014/0058210 A1* | 2/2014 | Raymond | A61B 17/02 600/215 |
| 2014/0135584 A1* | 5/2014 | Lee | A61N 1/0551 600/202 |
| 2015/0018627 A1* | 1/2015 | Vayser | A61B 1/32 600/213 |
| 2015/0057504 A1* | 2/2015 | Vayser | A61B 1/303 600/249 |
| 2015/0066428 A1* | 3/2015 | Larson | A61B 5/0555 702/155 |
| 2015/0250555 A1* | 9/2015 | Haverich | F21L 4/00 600/245 |
| 2016/0106466 A1* | 4/2016 | Gruber | A61B 1/303 606/193 |
| 2016/0361133 A1* | 12/2016 | Davis | A61B 90/35 |

* cited by examiner

LIGHTED POLYHEDRAL RETRACTOR

FIELD OF THE INVENTION

The present invention provides a surgical retractor that provides improved access to a surgical space, devised in the shape of a partial polyhedron, and also provides improved visualization of the surgical space with light emitting elements placed within the structure.

Typically, surgical retractors 'retract' something, that is, pull something 'open' along generally an "x" and "y" axis so that the user can see and have access to what is underneath. Surgical retraction is generally targeted to a specific tissue or a specific point. What has not heretofore been satisfactorily accomplished is expansion of a general work area around the area of interest, for example, not just limited to an "x" and "y" axis retraction, but even expansion of a general area along a plurality of axes. While that concept may not be possible in some surgical circumstances, it may be very desirable and possible in many instances. Specifically, it may be desirable to have a retractor that does not just merely retract one specific tissue or point of interest, but is capable of expanding a work area of interest in multiple dimensions in multiple ways creating the most suitable work environment possible. The instant invention accomplishes just that and provides an evenly illuminated environment also.

BACKGROUND

Surgical retractors are known. Surgical retractors that expand in place are known For example, U.S. Pat. No. 8,075,582 discloses an expandable intra-gastric balloon for treating obesity, the balloon being for implanting in the stomach in order to reduce its volume, said balloon comprising a first flexible pouch provided with first connection means for receiving a connection member that is for connection to a first fluid source in order to expand said first pouch in the stomach by filling it with fluid, the balloon being characterized in that it includes at least one second flexible pouch provided with second connection means, said second connection means being separate from the first connection means in such a manner as to be capable of being connected to a second fluid source different from the first fluid source. The invention applies to treating obesity.

In another example, U.S. Pat. No. 7,625,339 discloses a blade extending tower for setting blade depth on retractors having telescoping or extending blades. The blade extending tower features a base, a column extending from the base, and mating features on the column configured to engage the blades of a retractor to extend the blades to a desired blade depth. Blade depth of the retractor is set by sliding the retractor onto the blade extending tower such that the mating features of the blade extending tower engage the blades or the retractor, stopping the blades' progression while the rest of the retractor continues along the length of the column. Thus the blades of the retractor are extended from the retractor to a depth determined by the configuration of the blade extending tower.

In another example, U.S. Pat. No. 5,402,772 discloses an apparatus for retracting an organ inside the body to gain access to an adjacent tissue. The apparatus comprises an expandable cage and an expansion element. The expandable cage is capable of being inserted into the body through a small incision or puncture in a collapsed state. The expansion element is for selectively expanding the expansible cage inside the body to an expanded state. The expansion element includes an envelope enclosing a fluid-inflatable chamber. The expansible cage includes an additional envelope mounted inside the inflatable chamber and enclosing an additional fluid-inflatable chamber. The expansible cage is additionally capable of maintaining the expanded state independently of the expansion element after the expansible cage has been expanded by the expansion element to the expanded state.

In another example, U.S. Patent Application US2004/0236186 discloses an expandable surgical retractor for use in minimal incision surgery. The retractor consists of a fiber optic central rod surrounded by flexible wires designed to create an open space for visualization and surgical work within an illuminated surgical field. The flexible wires are disposed via selective pressure of the surgeon and are variable in number. The configuration will allow for both forward and back illumination of the surgical field. The expandable surgical retractor allows for surgical visualization in anatomical areas heretofore too complicated for surgical consideration. Other embodiments of the expandable surgical retractor are contemplated wherein a handle with an aperture may replace the central rod. The flexible wires may fit in openings around the aperture. The handle, in this embodiment, may have a light source and may be adapted to be used in select areas of anatomy. Further, the handle may be transparent. Thus, incorporating light sources into an expandable refractor are known.

In another example, U.S. Pat. No. 7,909,761 discloses methods and apparatus for a surgical retractor include a ring, a plurality of flexible straps connected to the ring, a patch of hook or loop material connected to each strap, a coordinating patch of hook or loop material connectable to the patient's skin or the surgical drape. The flexible straps of the surgical retractor may be frangibly connected together. LEDs molded into the distal end create a light source to illuminate the surgical site. The ring may take several forms including a flexible or adjustable ring and an inflatable bladder. The ring of the surgical retractor is inserted into the surgical incision, a patch of loop fastener is attached to the patient, a set of straps connected to the ring are pulled outward and the hook portion is applied to the loop portion to hold the incision open. The retractor is useable for thoracic and other types of surgery.

Many types of lights sources integrated with various retractor types are known. For example, U.S. Pat. No. 7,922,658 discloses a blade for a surgical retractor. The blade includes a base portion and a distal portion. The base portion may be attached to a frame of a surgical retractor. The distal portion may be removably coupled to the base portion and may be unitarily constructed of a translucent material. A light source may be removably coupled to the distal portion. The distal portion may be disposable.

In another example, U.S. Pat. No. 7,556,601 discloses methods and devices for illuminating a surgical space during surgery in a patient are provided. A retractor provides a working path for access to a location in the patient. A light instrument is positionable in working channel to emit light at the surgical space without substantially obstructing access to the surgical space.

In another example, U.S. Patent Application US2003/0095781 discloses illuminated surgical retractors include at least one retractor blade and a light delivery system. In some embodiments of the invention, the light delivery system includes a light emitter in the form of an elongated light emitting blade portion extending along the length of the retractor blade. The light emitter may be coupled to a light source integral with the retractor for illuminating all or a portion of the length of the light emitter or retractor blade.

In other embodiments of the invention, the light delivery system may include an array of lights which may be attached directly to the retractor blade or to a support in the shape of an elongated blade that extends along the length of the retractor blade for illuminating all or a portion of the length of the retractor blade.

Therefore, there remains an unmet need for the device of the invention of the present application that provides improved unobstructed free and direct access to an evenly dimensioned surgical area with full geometrically even illumination providing the surgeon heretofore unfettered views and access to critical surgical environments.

SUMMARY OF THE INVENTION

The present invention provides a surgical retractor that provides improved access to a surgical space. Specifically, the instant invention provides a surgical retractor that is devised in the shape of a partial polyhedron, mechanically implemented by placing at a designated area and then expanding along one or more of its partial polyhedral axes to uniformly retract the designated body tissues and expand the accessible surgical space while also providing improved visualization of the surgical field with strategically placed light emitting elements at specific locations along the partial polyhedral framework.

DETAILED DESCRIPTION

For clarity of disclosure, and not by way of limitation, the detailed description of the invention is divided into the following subsections that describe or illustrate certain features, embodiments or applications of the present invention.

Definitions

A "surgical retractor" as used herein refers to an instrument for retaining the edges of a surgical incision or organ or other tissue to allow access to a desired area for a surgical procedure.

A "light-emitting element" as used herein refers to any suitable device for providing illumination directly or indirectly to the surgical space.

THE DEVICE OF THE PRESENT INVENTION

In one embodiment the present invention provides a surgical retractor:
 i. comprising a structure formed with legs that upon deployment, expand into a partial polyhedral shape;
 ii. said structure being compact in its non-deployed state and upon deployment, unfolds its legs to expand allowing for said deployment to simultaneously and in a plurality of directions retract a specific body tissue area;
 iii. said deployment initiated and controlled by the user.

In one embodiment, the surgical refractor of the present invention will also contain light emitting elements.

In one embodiment, the partial polyhedral shape is a partial icosahedron.

Figure 4:
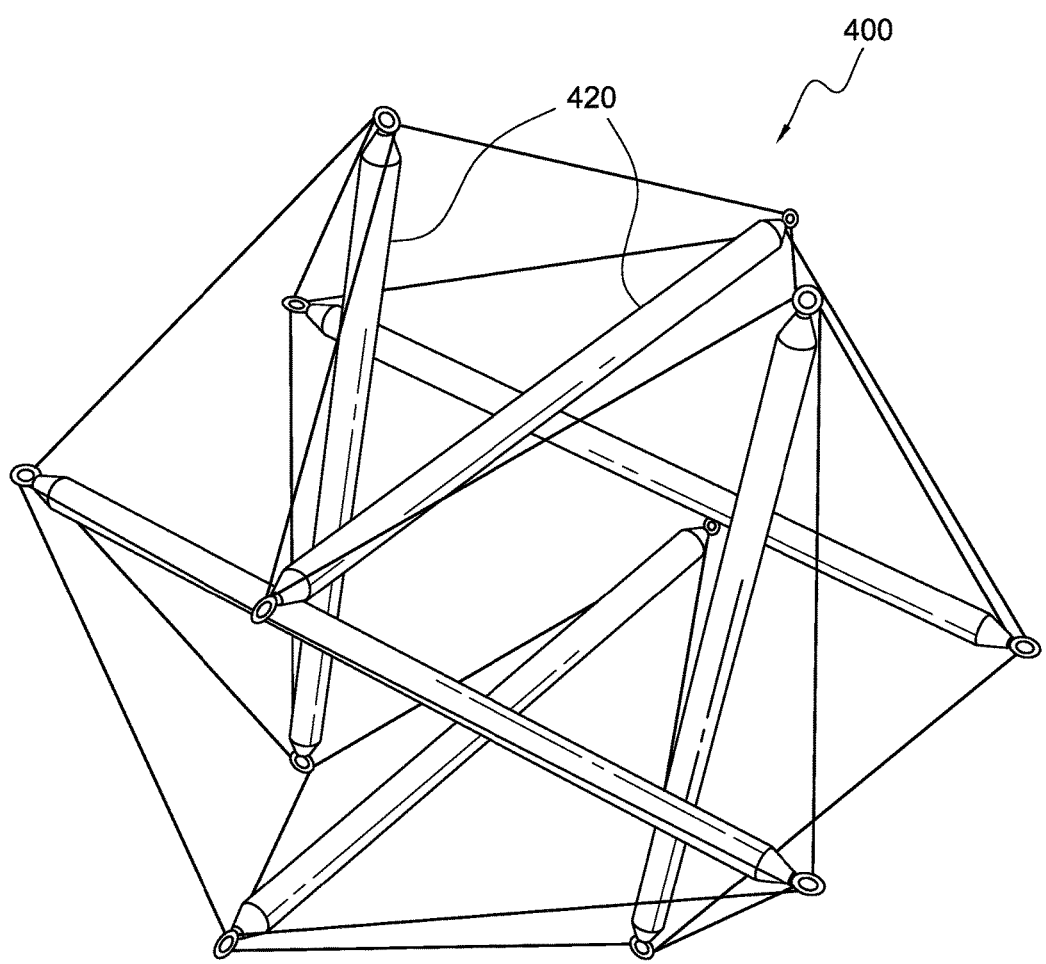
FIG. 4 shows one manner of implementing the folding and unfolding of the legs that form a polyhedral structure through the use of guide wires.

In one embodiment, the deployment of the retractor of the present invention is achieved substantially by the method disclosed in FIG. 4. FIG. 4 shows a structure 400 having a plurality of legs 420 in accordance with an embodiment.

Figure 5:
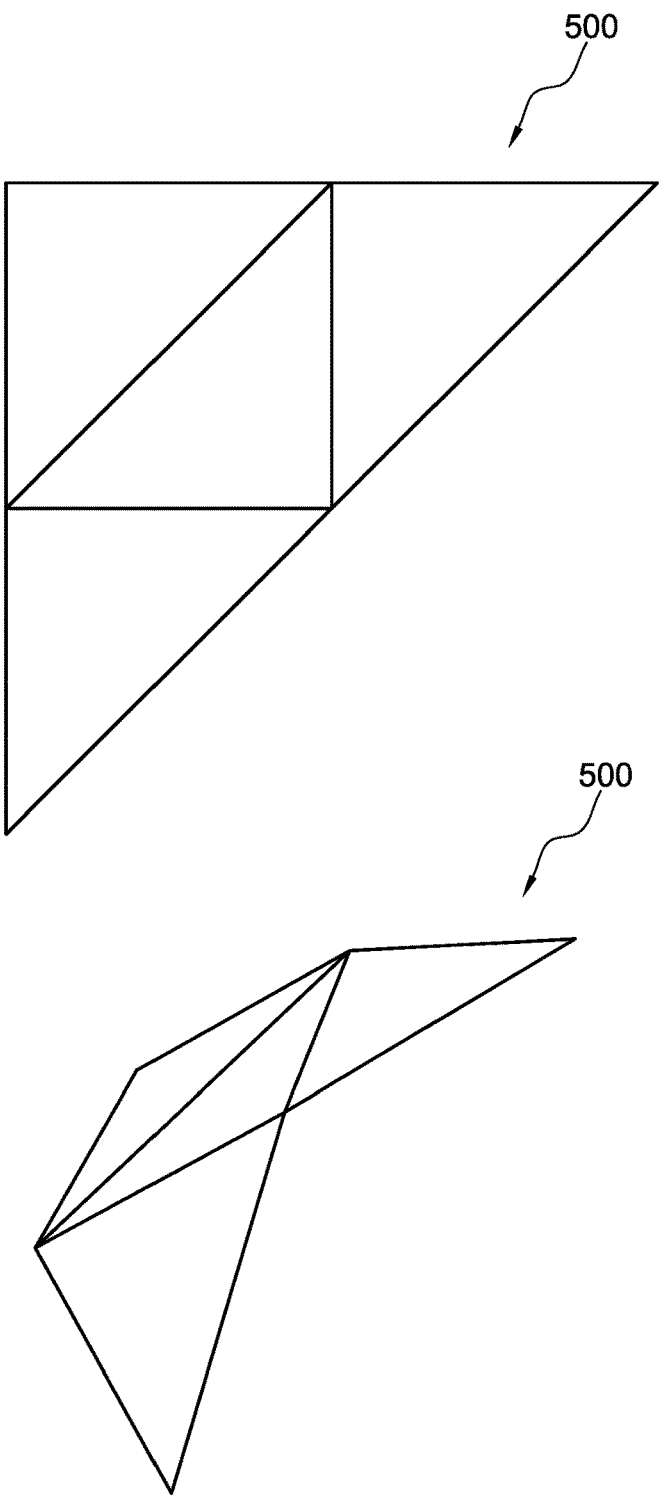
FIG. 5 shows and alternative manner of implementing the folding and unfolding of the legs that form a polyhedral structure through the use of hinged axes.

In one embodiment, the deployment of the retractor of the present invention is achieved substantially by the method disclosed in FIG. 5. FIG. 5 shows a retractor 500 in a folded (non-deployed) state and in an unfolded (deployed) state.

In one embodiment, the deployment of the retractor of the present invention is achieved substantially by a combination of the methods disclosed in FIGS. 4 and 5.

In one embodiment, the deployment of the retractor of the present invention is achieved by methods known by those skilled in the art.

In one embodiment, the legs of the device of the present invention are made from surgical grade steel.

In one embodiment, the legs of the device of the present invention are made from surgical grade materials other than steel, including but not limited to ceramics and plastics.

In one embodiment, the legs of the device of the present invention are hollow to allow for conduit to supply energy to light emitting elements.

In one embodiment, the device of the present invention is single use.

In one embodiment, the light emitting elements are self powered.

In one embodiment, the light emitting elements are replaceable.

In one embodiment, the light emitting elements are mounted magnetically.

In one embodiment, the light emitting elements may be user arranged.

In one embodiment, once deployed, the retractor of the present invention further comprises a locking mechanism.

In one embodiment, the locking mechanism can be unlocked whereupon the retractor may be reversibly deconstructed to allow for removal from the body cavity area where deployed.

In one embodiment, once deployed, the retractor of the present invention compacts along one or more of its partial polyhedral axes by reversibly folding the legs that form the polyhedral structure.

In one embodiment, the retractor of the present invention compacts into a substantially linear shape such that said refractor could be placed and withdrawn through a laparscopic trocar and deployed robotically and usable in laparscopic and robotic surgical procedures.

EXAMPLES

For clarity of disclosure, the following examples are based on this device implemented in connection with a typical thyroid surgery. One of ordinary skill in the art will appreciate the many applications and embodiments of the device of the present invention, for example, and not by way of limitation, any surgery that is largely internal where access is difficult, surgical spaces are confined, and surrounding tissues are delicate.

Thyroid surgery requires steady retraction throughout the procedure. Typically, surgical assistants manually provide such retraction. There have been attempts at providing self-retaining retraction. For example, a retractor made from K-wire is bent in the shape of a hook with a blunted tip and placed at the area where the tissue will be retracted. A small loop is formed at the end of the shaft of the steel wire to hold a rubber band which is attached to an ordinary pair of forceps. The forceps are fixed to an immobile part of the surgical drape providing force to the K-wire hook and providing steady retraction.

Other more specifically tailored devices have been tried. For example, the MASTR™ retractor by Surgical Innovations provides a self-retaining disposable thyroid surgery retractor which is capable of retracting the platysma muscle and strap muscles and conforms to the anatomy of the neck area and provides six direction refraction.

These methods provide uneven distribution of force. Moreover, during thyroid surgery, the optimal surgical space is a moving target as different parts of the thyroid being visible during different portions of the surgery is desirable.

The thyroid gland is located at the front of the neck, surrounded by various muscles and fatty tissues. It has two lobes that are located on each side of the trachea and are joined at the center by a bridge of thyroid tissue known as the isthmus.

Scarring from thyroid surgery is extremely visible since the incision is made on the front portion of the neck. Trauma from uneven retractor force can be a source of scarring.

Attempts have been made to provide O-ring devices common in abdominal surgeries which is a device constructed of two rings connected by a plastic material such as polyurethane. An O-ring distributes force evenly around its circumference. However, where the surgical site is not ideally perfectly round, or where the surgical site is not as deep as an abdominal surgery, bunching of the plastic material may occur obstructing the surgical field.

Moreover, none of these designs provide for a direct source of light at or near the surgical field which means that the light provided to the surgical field must come from a source further away subject to obstruction.

The device of the present invention overcomes all these negative attributes and combines all of the positive attributes.

Firstly, the construction is in the shape of a partial polyhedron, i.e., may have any number of retraction loci which provides for force uniformity of a chosen degree depending on the shape of the surgical field in a given instance.

The retraction is implemented by deploying in place and expanding and locking at the desired retraction level providing even and constant retraction force.

The retraction may be reversed by unlocking the locking mechanism and reversibly contracting the legs of the device uniformly at a desired speed.

Figure 1:
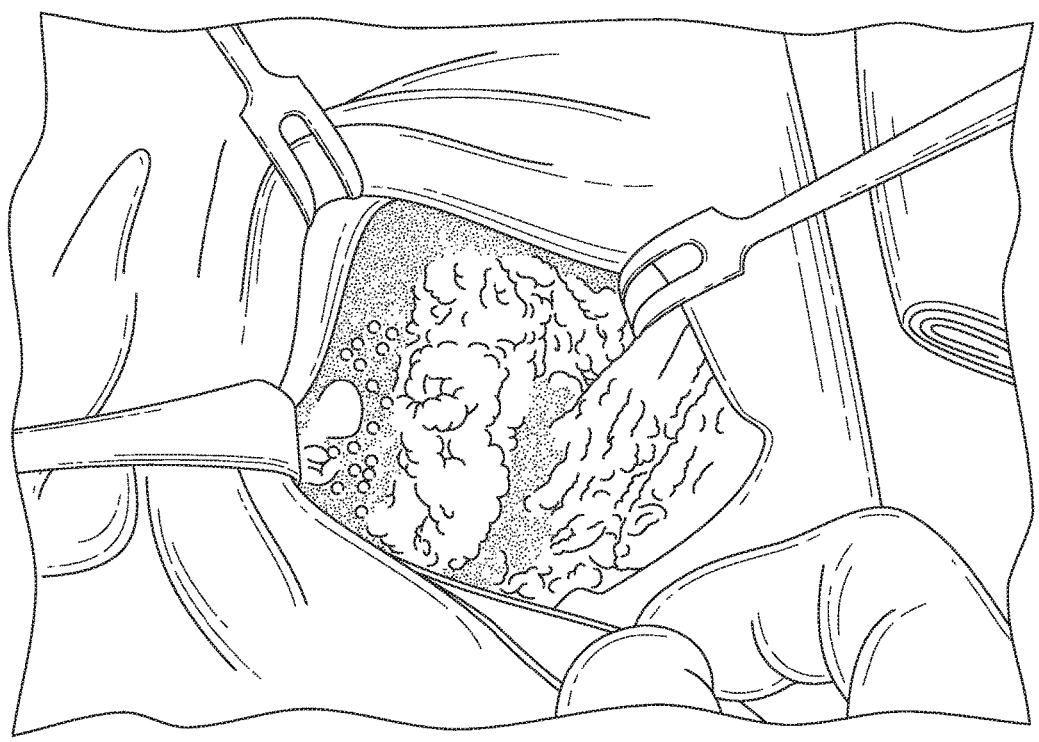
FIG. 1 shows a conventional surgical space created by the use of traditional surgical instruments restraining surface tissues in a single direction to expose underlying tissues.
Figure 2:
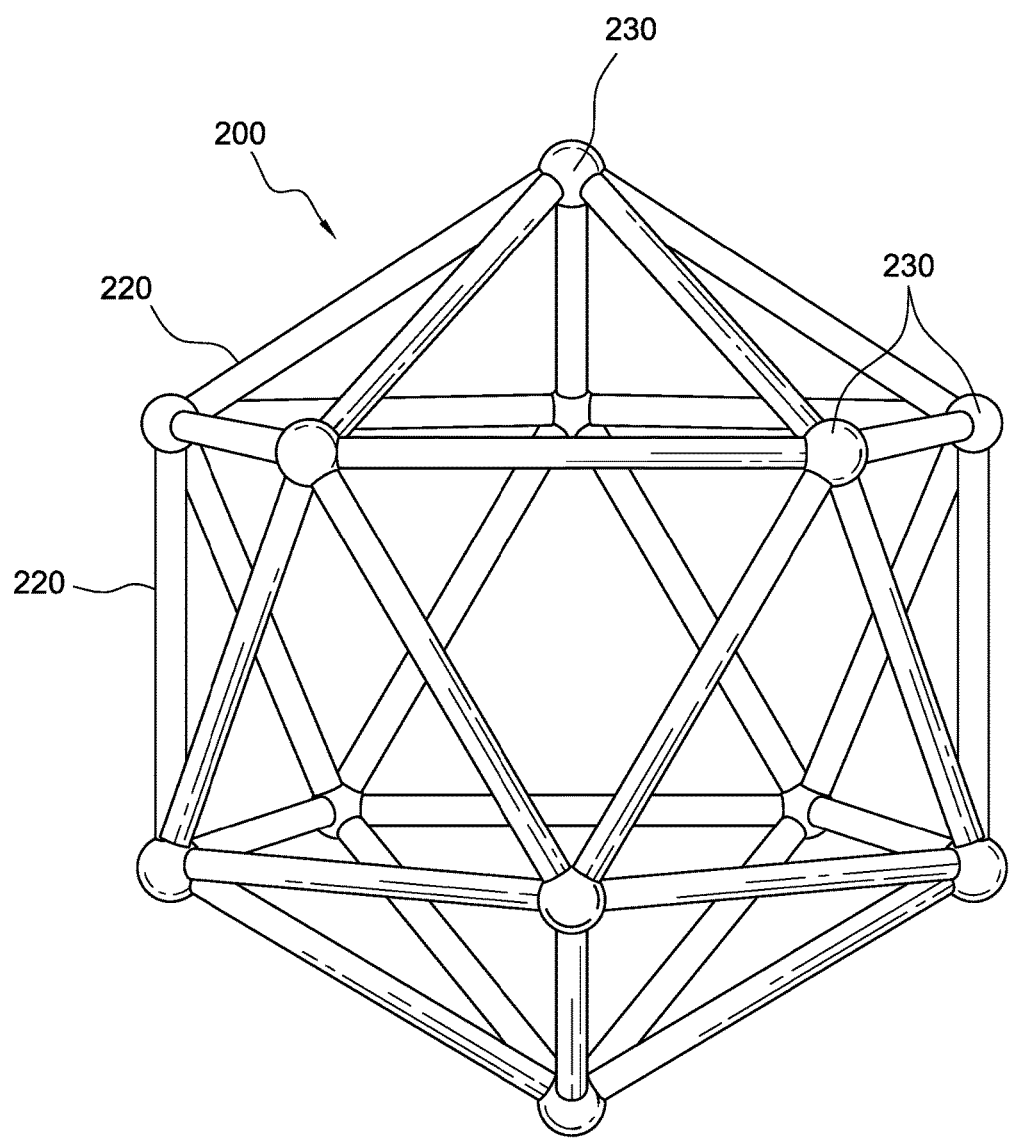
FIG. 2 shows a basic polyhedral structure further depicting how lighting elements could be placed at points along the polyhedral framework.
Figure 3:
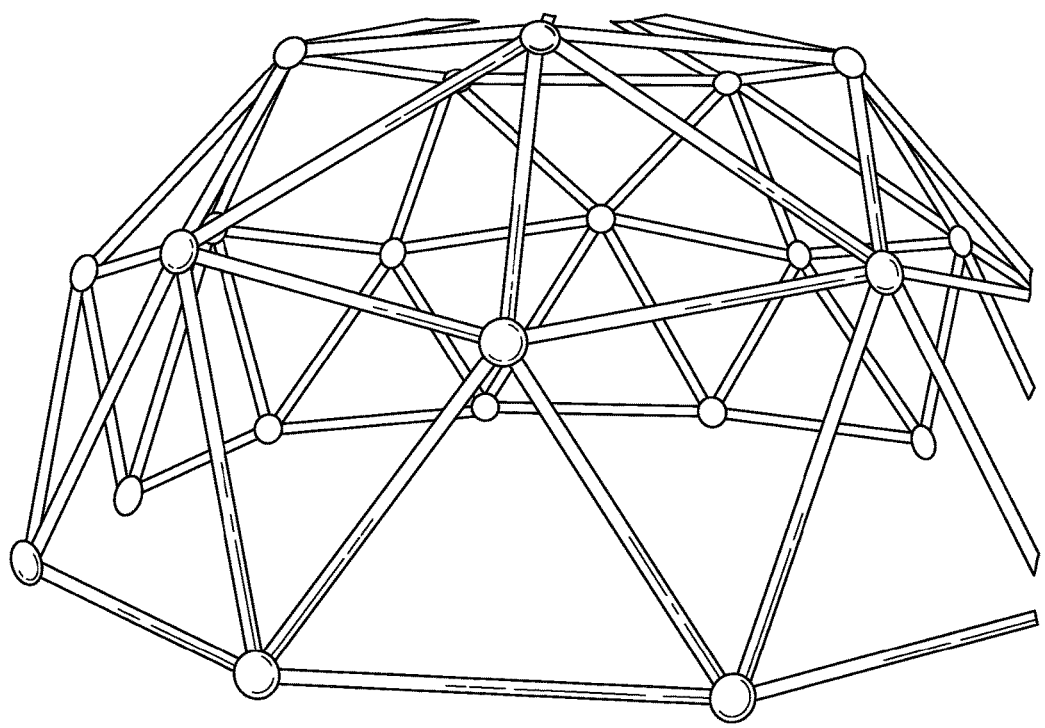
FIG. 3 shows how a polyhedral structure can be partially implemented to create/expand a defined space.

The retractor of the device of the present invention is mechanical and may be implemented with hollow legs which allows for light emitting elements to be implemented at the retraction site directly providing for an even, constant and illuminated retraction creating the optimal surgical field. For example FIG. 2 shows structure 200 having a plurality of legs 220 and a plurality of light-emitting elements 230 in accordance with an embodiment.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

Each and every feature described herein, and each and every combination of two or more of such features, is included within the scope of the present invention provided that the features included in such a combination are not mutually exclusive.

What is claimed is:

1. A surgical retractor comprising:
   a structure comprising a plurality of legs, said structure having an expanded state and a non-expanded state, wherein the structure has an icosahedron shape having a plurality of retraction loci when in the expanded state, wherein each retraction locus is located at a point defined by an end of one of the plurality of legs;
   a plurality of light-emitting elements, each light-emitting element being located at a respective retraction locus of the structure, wherein each of the plurality of retraction loci includes a respective light-emitting element;
   wherein said structure is compact when in the non-expanded state, wherein the structure is adapted to expand in a plurality of directions when transforming from the non-expanded state to the expanded state and thereby to retract a specific body tissue area; and
   wherein transformation from the non-expanded state to the expanded state occurs in response to an action by a user and is controlled by the user.

2. The surgical retractor of claim 1, wherein each of the plurality of legs comprises surgical grade steel.

3. The surgical retractor of claim 1, wherein each of the plurality of legs comprises a material chosen from the following group: ceramic, plastic, surgical grade metal alloy, and carbon fiber.

4. The surgical retractor of claim 1, wherein the surgical retractor has a linear characteristic when in the non-expanded state.

5. The surgical retractor of claim 1, wherein:
   the structure defines a symmetrical volume within the structure when in the expanded state;
   when the structure is disposed inside a body of a patient and is in the expanded state, the symmetrical volume provides an accessible surgical area.

\* \* \* \* \*